United States Patent
Ishihara

(10) Patent No.: US 9,498,109 B2
(45) Date of Patent: Nov. 22, 2016

(54) FLUORESCENCE ENDOSCOPE DEVICE

(75) Inventor: Yasushige Ishihara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 533 days.

(21) Appl. No.: 13/565,440

(22) Filed: Aug. 2, 2012

(65) Prior Publication Data
US 2012/0302893 A1 Nov. 29, 2012

Related U.S. Application Data

(63) Continuation of application No. PCT/JP2011/051445, filed on Jan. 26, 2011.

(30) Foreign Application Priority Data

Feb. 10, 2010 (JP) ................................ 2010-027886

(51) Int. Cl.
*A61B 6/00* (2006.01)
*A61B 1/00* (2006.01)
(Continued)

(52) U.S. Cl.
CPC ....... *A61B 1/00186* (2013.01); *A61B 1/00009* (2013.01); *A61B 1/043* (2013.01);
(Continued)

(58) Field of Classification Search
CPC .................................................. A61B 1/00186
See application file for complete search history.

(56) References Cited

U.S. PATENT DOCUMENTS

| | | | |
|---|---|---|---|
| 6,537,211 B1* | 3/2003 | Wang et al. | 600/178 |
| 2003/0001104 A1* | 1/2003 | Sendai | A61B 1/00009 250/458.1 |

(Continued)

FOREIGN PATENT DOCUMENTS

| | | |
|---|---|---|
| EP | 2 108 300 A1 | 10/2009 |
| JP | 62-247232 A | 10/1987 |

(Continued)

OTHER PUBLICATIONS

Bolte et al., "A guided tour into subcellular colocalization analysis in light microscopy", The Royal Microscopical Society, 2006, pp. 213-232.*

(Continued)

*Primary Examiner* — Christopher Cook
(74) *Attorney, Agent, or Firm* — Scully, Scott, Murphy & Presser, PC

(57) ABSTRACT

Provided is a fluorescence endoscope device that includes a light source; an image generating portion that captures an image of fluorescence generated at a subject due to irradiation with excitation light to obtain a fluorescence image and that captures an image of return light returning from the subject due to irradiation with white light to obtain a white-light image; a dividing portion that divides the fluorescence image by the white-light image to generate a divided fluorescence image; a coordinate extracting portion that extracts a second region of the divided fluorescence image having a gradation value higher than a second threshold; a fluorescence-image correcting portion that extracts a first region having a gradation value higher than a first threshold in the fluorescence image and generates a corrected fluorescence image in which an overlap region that overlaps the second region is extracted; and a monitor that displays the corrected fluorescence image.

9 Claims, 12 Drawing Sheets

(51) Int. Cl.
  *A61B 1/04* (2006.01)
  *A61B 1/05* (2006.01)
  *A61B 1/06* (2006.01)
  *A61B 5/00* (2006.01)
  *G01N 21/64* (2006.01)

(52) U.S. Cl.
  CPC .............. *A61B 1/05* (2013.01); *A61B 1/0638* (2013.01); *A61B 1/0646* (2013.01); *A61B 5/0071* (2013.01); *A61B 5/0084* (2013.01); *G01N 21/6456* (2013.01)

(56) References Cited

U.S. PATENT DOCUMENTS

| | | | |
|---|---|---|---|
| 2004/0210138 A1* | 10/2004 | Murashita | A61B 8/08 600/443 |
| 2010/0049058 A1 | 2/2010 | Ishihara | |
| 2010/0080459 A1* | 4/2010 | Dai et al. | 382/170 |

FOREIGN PATENT DOCUMENTS

| | | | |
|---|---|---|---|
| JP | 3-058279 A | 3/1991 | |
| JP | 2003-036436 A | 2/2003 | |
| JP | 2006-175052 A | 7/2006 | |
| JP | 2007-215927 A | 8/2007 | |
| JP | 2008-154846 A | 7/2008 | |

OTHER PUBLICATIONS

European Search Report dated Nov. 9, 2012 from corresponding European Patent Application No. EP 11 74 2110.7.
International Search Report dated Apr. 12, 2011 issued in PCT/JP2011/051445.

* cited by examiner

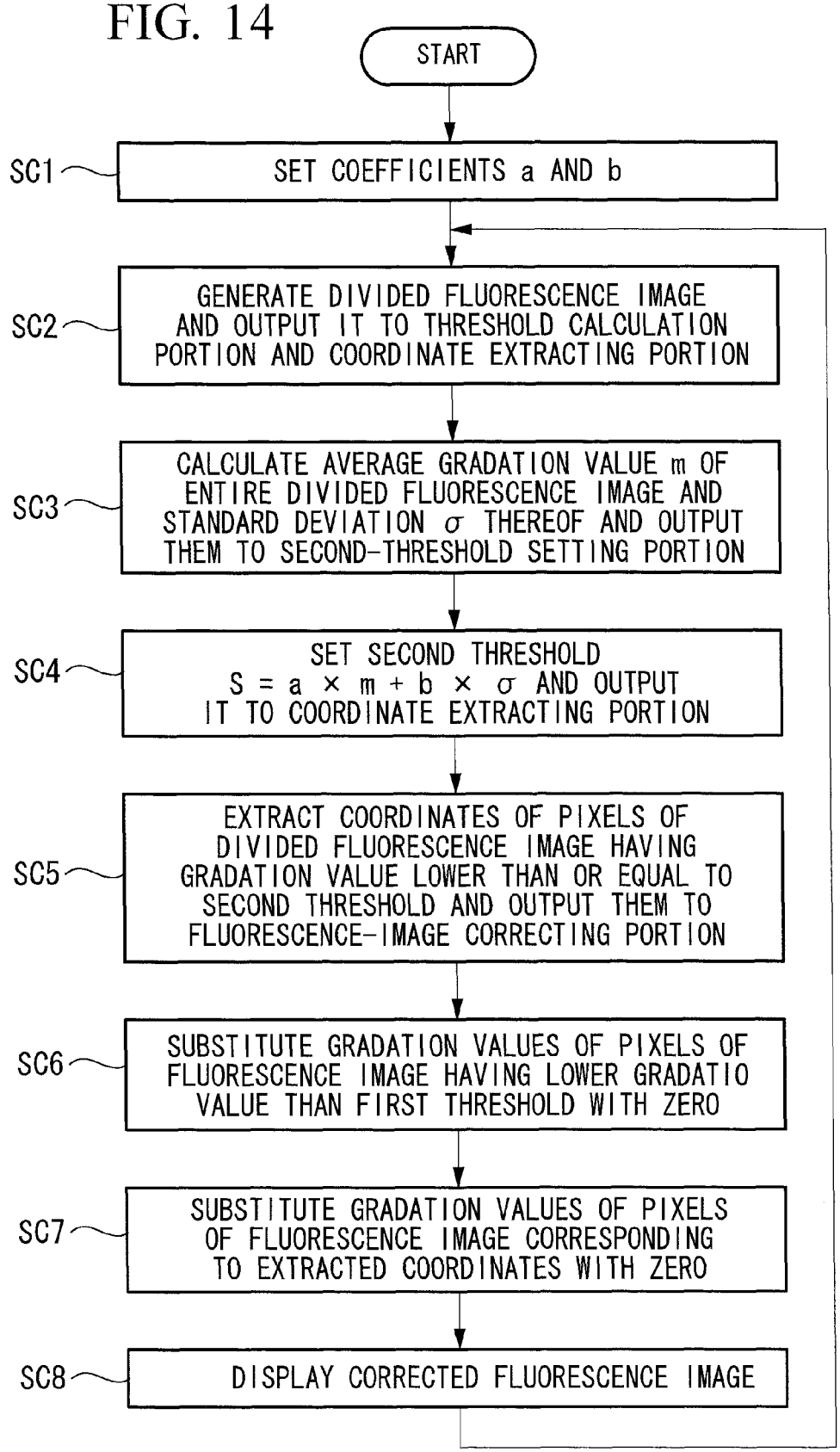

FLUORESCENCE ENDOSCOPE DEVICE

CROSS-REFERENCE TO RELATED APPLICATIONS

This is a continuation of International Application PCT/JP2011/051445, with an international filing date of Jan. 26, 2011, which is hereby incorporated by reference herein in its entirety. This application claims the benefit of Japanese Patent Application No. 2010-027886, the contents of which are incorporated herein by reference.

TECHNICAL FIELD

The present invention relates to fluorescence endoscope devices.

BACKGROUND ART

A known fluorescence endoscope device in the related art can obtain a bright fluorescence image of a diseased site by irradiating an observation target site doped with a fluorochrome that preferentially accumulates in a diseased site, such as a cancer cell, with excitation light for exciting the fluorochrome to generate drug fluorescence and by capturing an image of the drug fluorescence (for example, see PTL 1). The fluorescence endoscope device disclosed in PTL 1 corrects variations in fluorescence intensity of a fluorescence image, which depends on the observation distance, the observation angle, etc., by dividing a fluorescence image, which is obtained from an observation target site irradiated with excitation light and is based on the fluorescence intensity, by a reference image, which is obtained from the same observation target site irradiated with reference light and is based on the intensity of the reflected light, to obtain a quantitative divided fluorescence image.

CITATION LIST

Patent Literature

{PTL 1} Japanese Unexamined Patent Application, Publication No. 2006-175052

SUMMARY OF INVENTION

An aspect of the present invention is a fluorescence endoscope device including a light source that irradiates a subject with excitation light and illumination light; a fluorescence-image acquisition portion that captures an image of the fluorescence generated at the subject due to the irradiation with the excitation light from the light source to obtain a fluorescence image; a reference-image acquisition portion that captures an image of return light returning from the subject due to the irradiation with the illumination light from the light source to obtain a reference image; a divided-fluorescence-image generating portion that divides the fluorescence image by the reference image to generate a divided fluorescence image; a first-region extracting portion that extracts a first region having a gradation value higher than a first threshold in the fluorescence image; a second-region extracting portion that extracts a second region having a gradation value higher than a second threshold in the divided fluorescence image; a corrected-fluorescence-image generating portion that generates a corrected fluorescence image in which an overlap region, where the first region of the fluorescence image extracted by the first-region extracting portion overlaps the second region of the divided fluorescence image extracted by the second-region extracting portion, is extracted from the fluorescence image; and a display portion that displays the corrected fluorescence image generated by the corrected-fluorescence-image generating portion.

In the above-described aspect, the fluorescence endoscope device may further include a threshold input portion for inputting the first threshold and the second threshold.

Furthermore, in the above-described aspect, the fluorescence endoscope device may further include a first-threshold setting portion that sets the first threshold on the basis of a sum of an average gradation value of each of pixels of the fluorescence image and a standard deviation of that gradation value. Furthermore, the first-threshold setting portion may set the first threshold on the basis of a sum of a modal gradation value of each of pixels of the fluorescence image and a standard deviation of that gradation value, or may set the first threshold on the basis of a sum of a median gradation value of each of pixels of the fluorescence image and a standard deviation of that gradation value.

Furthermore, in the above-described aspect, the fluorescence endoscope device may further include a second-threshold setting portion that sets the second threshold on the basis of a sum of an average gradation value of each of pixels of the divided fluorescence image and a standard deviation of that gradation value. Furthermore, the second-threshold setting portion may set the second threshold on the basis of a sum of a modal gradation value of each of pixels of the divided fluorescence image and a standard deviation of that gradation value, or may set the second threshold on the basis of a sum of a median gradation value of each of pixels of the divided fluorescence image and a standard deviation of that gradation value.

Furthermore, in the above-described aspect, the fluorescence endoscope device may further include an endoscope scope including, at a tip thereof, a light-emitting portion that emits the excitation light and the reference light and a light-receiving portion that receives the fluorescence and the return light; and a threshold setting portion that sets the first threshold and the second threshold on the basis of scope information about the light-emitting portion and the light-receiving portion of the endoscope scope.

Examples of the scope information include the number of light-emitting portions and the observation angles of the light-emitting portion and light-receiving portion.

BRIEF DESCRIPTION OF DRAWINGS

FIG. 14 is a flowchart showing the operation of the fluorescence endoscope device in FIG. 13.

DESCRIPTION OF EMBODIMENTS

A fluorescence endoscope device according to an embodiment of the present invention will be described below with reference to the drawings.

Figure 1:
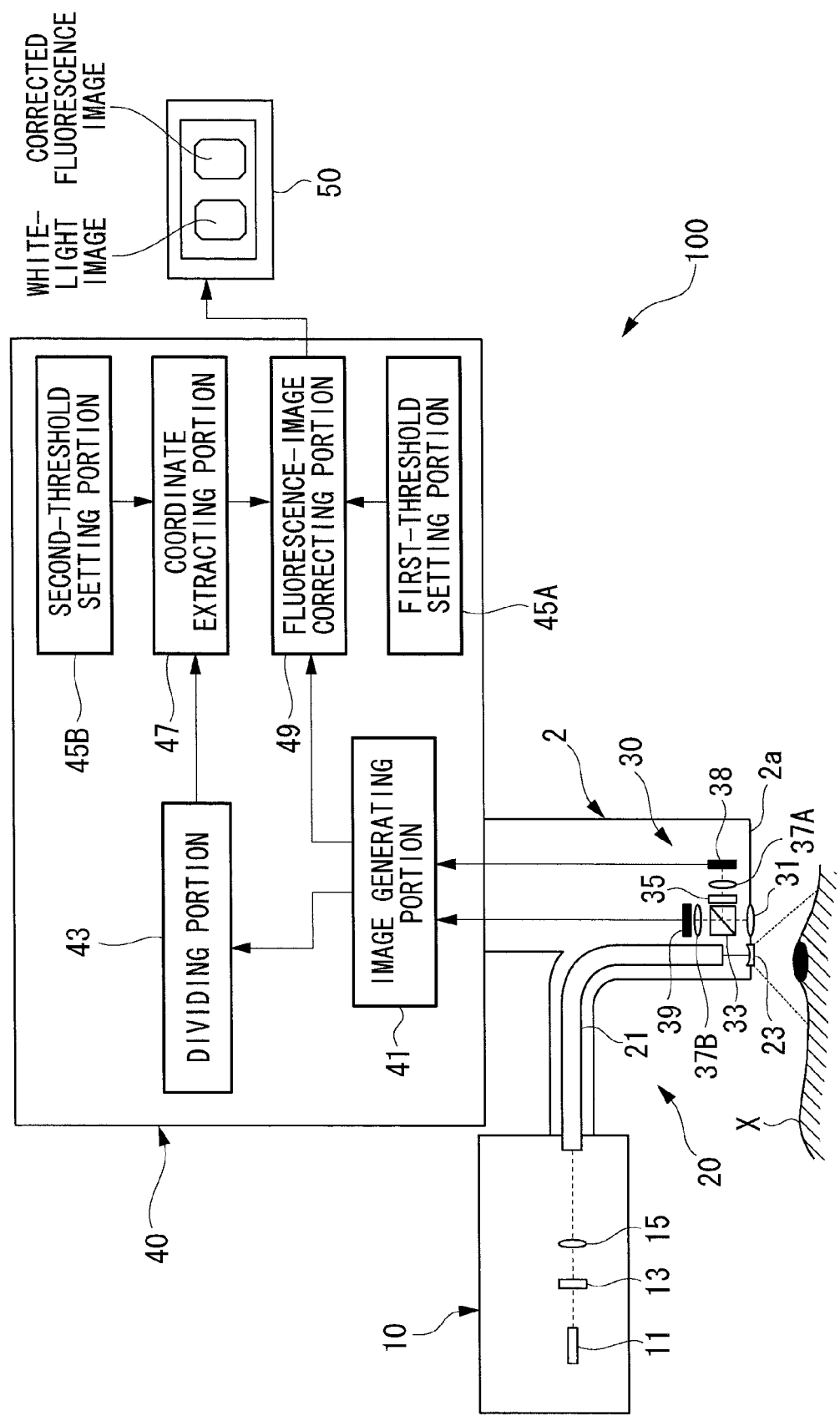
FIG. 1 is a schematic block diagram of a fluorescence endoscope device according to an embodiment of the present invention.

As shown in FIG. 1, a fluorescence endoscope device 100 according to this embodiment includes a long, thin scope 2 to be inserted into a body cavity, an illuminating unit 20 including a light source 10 that emits illumination light from a tip 2a of the scope 2, an image-capturing unit 30 disposed in the scope 2 to obtain image information of an observation target site X, i.e., a subject, an image-processing section 40 that processes the image information obtained by the image-capturing unit 30, and a monitor 50 (display portion) on which the image and image information processed by the image-processing section 40 are displayed.

The light source 10 includes a xenon lamp (Xe lamp) 11 that emits illumination light, an excitation light filter 13 that separates white light (reference light) containing excitation light from the illumination light emitted from the xenon lamp 11, and a coupling lens 15 that collects the white light containing the excitation light, separated by the excitation light filter 13. The excitation light filter 13 separates white light containing excitation light with a wavelength band of, for example, from 400 nm to 740 nm.

Furthermore, the illuminating unit 20 includes a light-guide fiber 21 disposed substantially over the overall length of the scope 2 in the longitudinal direction, and a spreading lens 23 disposed at the tip 2a of the scope 2.

The light-guide fiber 21 guides the white light containing the excitation light, collected by the coupling lens 15, to the tip 2a of the scope 2. The spreading lens 23 spreads the white light containing the excitation light, guided by the light-guide fiber 21, to illuminate the observation target site X.

The image-capturing unit 30 includes an objective lens 31 that collects return light returning from the observation target site X irradiated with the white light containing the excitation light by the illuminating unit 20, and a beam splitter 33 that splits the return light, collected by the objective lens 31, according to the wavelength.

The objective lens 31 is disposed beside the spreading lens 23 at the tip 2a of the scope 2. In the return light, the beam splitter 33 reflects light (excitation light and fluorescence) having a longer wavelength than the excitation wavelength and allows white light (return light) that has a shorter wavelength than the excitation wavelength to pass therethrough.

This image-capturing unit 30 includes an excitation-light cut filter 35 that, of the excitation light and fluorescence reflected by the beam splitter 33, blocks excitation light and allows only fluorescence (for example, near-infrared fluorescence) to pass therethrough, a focusing lens 37A that focuses fluorescence passing through the excitation-light cut filter 35, a focusing lens 37B that focuses white light passing through the beam splitter 33, a fluorescence-image-capturing portion 38 that captures an image of the fluorescence focused by the focusing lens 37A, and a white-light image-capturing portion 39 that captures an image of the white light focused by the focusing lens 37B.

For example, the excitation-light cut filter 35 allows only fluorescence in the wavelength band from 765 nm to 850 nm to pass therethrough. The fluorescence-image-capturing portion 38 is, for example, a highly sensitive monochrome CCD for fluorescence. This fluorescence-image-capturing portion 38 obtains fluorescence image information by capturing an image of fluorescence. The white-light image-capturing portion 39 is, for example, a color CCD for white light and has a mosaic filter (not shown). This white-light image-capturing portion 39 obtains white-light image information by capturing an image of white light.

The image-processing section 40 includes an image generating portion (a fluorescence-image acquisition portion and a reference-image acquisition portion) 41 that generates a fluorescence image and a white-light image (reference image), and a dividing portion (divided-fluorescence-image generating portion) 43 that divides the fluorescence image generated by the image generating portion 41 by the white-light image.

The image generating portion 41 generates a two-dimensional fluorescence image from the fluorescence image information obtained by the fluorescence-image-capturing portion 38 and generates a two-dimensional white-light image from the white-light image information obtained by the white-light image-capturing portion 39. The dividing portion 43 divides the fluorescence image of the observation target site X by the white-light image of the same observation target site X to generate a divided fluorescence image, in which the variation in fluorescence intensity of the fluorescence image, which depends on the observation distance, the observation angle, etc., is reduced.

Furthermore, the image-processing section 40 includes a first-threshold setting portion 45A that sets a first threshold of the gradation value of the fluorescence image, a second-threshold setting portion 45B that sets a second threshold of the gradation value of the divided fluorescence image generated by the dividing portion 43, a coordinate extracting portion 47 (a second-region extracting portion) that extracts predetermined coordinates of pixels of the divided fluorescence image, and a fluorescence-image correcting portion (a first-region extracting portion and a corrected-fluorescence-image generating portion) 49 that corrects the fluorescence image.

The first-threshold setting portion 45A sets, as the first threshold, a threshold for removing a low-gradation region in the fluorescence image, such as a background, resulting from faint fluorescence emitted from a healthy site of the observation target site X. Furthermore, the first-threshold setting portion 45A outputs the set first threshold to the fluorescence-image correcting portion 49.

The second-threshold setting portion 45B sets, as the second threshold, a threshold for removing a low-gradation region in the divided fluorescence image, such as a background of the observation target site X. Furthermore, the second-threshold setting portion 45B outputs the set second threshold to the coordinate extracting portion 47.

The coordinate extracting portion 47 extracts the coordinates of the pixels of the divided fluorescence image having a gradation value lower than or equal to the second threshold inputted from the second-threshold setting portion 45B. Furthermore, the coordinate extracting portion 47 outputs the extracted coordinates to the fluorescence-image correcting portion 49.

The fluorescence-image correcting portion 49 performs correction such that the gradation values of the pixels of the fluorescence image having a lower gradation value than the first threshold inputted from the first-threshold setting portion 45A are substituted with zero. Furthermore, the fluorescence-image correcting portion 49 performs correction such that the gradation values of the pixels of the corrected fluorescence image having the same coordinates as the coordinates extracted by the coordinate extracting portion 47 are substituted with zero. As a result, a corrected fluorescence image obtained by correcting the fluorescence image twice is generated. Furthermore, the fluorescence-image correcting portion 49 sends the generated corrected fluorescence image to the monitor 50, along with the white-light image and the fluorescence image.

The monitor 50 can simultaneously display the white-light image and the fluorescence image or the corrected fluorescence image sent from the fluorescence-image correcting portion 49.

Figure 2:
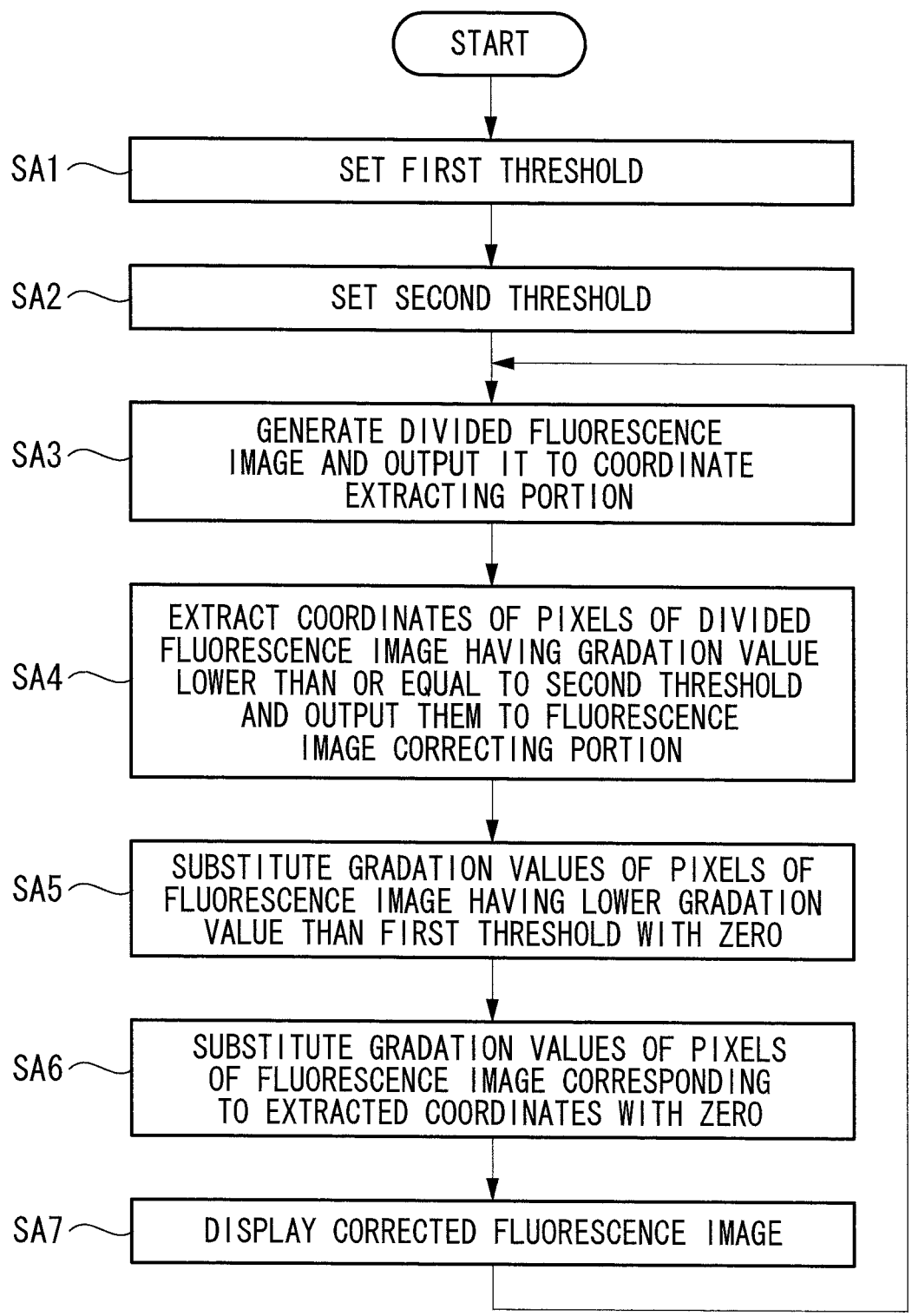
FIG. 2 is a flowchart showing the operation of the fluorescence endoscope device in FIG. 1.

The operation of the thus-configured fluorescence endoscope device 100 according to this embodiment will be described with reference to the flowchart shown in FIG. 2.

When an observation target site X inside the body cavity of a living body is observed using the fluorescence endoscope device 100 according to this embodiment, a fluorescence agent that preferentially accumulates in a diseased site, such as a cancer cell, is attached to or caused to be absorbed in the observation target site X.

Then, the first-threshold setting portion 45A sets the first threshold (step SA1) and outputs the first threshold to the fluorescence-image correcting portion 49. Furthermore, the second-threshold setting portion 45B sets the second threshold (step SA2) and outputs the second threshold to the coordinate extracting portion 47.

Figure 3:
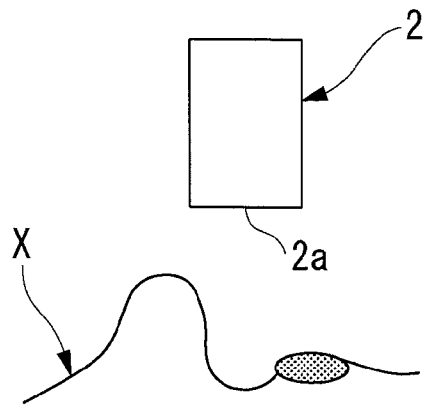
FIG. 3 is a diagram showing a state in which a scope of the fluorescence endoscope device in FIG. 1 is arranged to face an observation target site.

Next, the scope 2 is inserted into the body, and the tip 2a is made to face the observation target site X, as shown in FIG. 3. By activating the light source 10 in this state, white light containing excitation light, which is emitted from the xenon lamp 11 and is separated by the excitation light filter 13, is collected by the coupling lens 15 and is guided to the tip 2a of the scope 2 by the light-guide fiber 21. This white light is spread by the spreading lens 23 and illuminates the observation target site X.

At the observation target site X, the fluorescence agent attached thereto or caused to be absorbed therein is excited by the excitation light and emits fluorescence, and portions of the white light and the excitation light are reflected at the surface. The fluorescence, the white light, and the excitation light are collected by the objective lens 31, and the beam splitter 33 reflects light having a longer wavelength than the excitation wavelength, i.e., excitation light and fluorescence, and allows the white light that has a shorter wavelength than the excitation wavelength to pass therethrough.

The excitation light and fluorescence reflected by the beam splitter 33 are incident on the excitation-light cut filter 35, where the excitation light is removed. Then, only the fluorescence is focused by the focusing lens 37A, and the fluorescence-image-capturing portion 38 captures the image thereof. Thus, the fluorescence-image-capturing portion 38 obtains the fluorescence image information of the observation target site X. The white light passing through the beam splitter 33 is focused by the focusing lens 37B, and the image thereof is captured by the white-light image-capturing portion 39. Thus, the white-light image-capturing portion 39 obtains the white-light image information of the observation target site X. Either of the fluorescence image information and the white-light image information may be obtained first; or they may be obtained simultaneously.

Figure 4A:
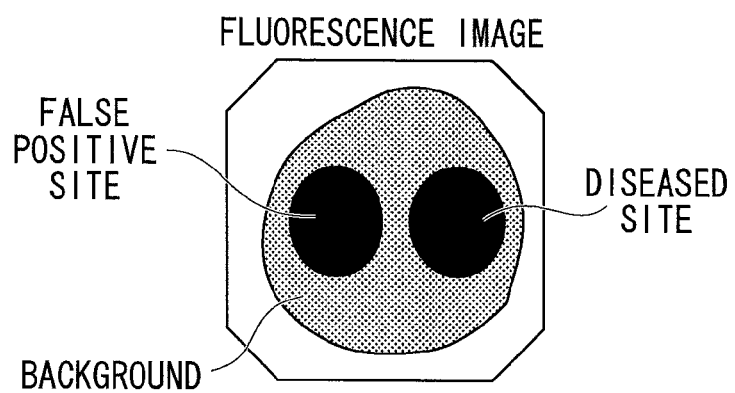
FIG. 4A is a diagram showing an example of a fluorescence image.

The fluorescence image information obtained by the fluorescence-image-capturing portion 38 and the white-light image information obtained by the white-light image-capturing portion 39 are inputted to the image generating portion 41 of the image-processing section 40. The image generating portion 41 generates a two-dimensional fluorescence image, as shown in FIG. 4A, on the basis of the fluorescence image information and generates a two-dimensional white-light image on the basis of the white-light image information. The generated fluorescence image and white-light image are sent to the monitor 50 to be displayed via the fluorescence-image correcting portion 49.

In reality, because a fluorescence agent accumulates not only in a diseased site but also in a small amount in a healthy site, faint fluorescence is emitted also from areas other than the diseased site. The faint fluorescence emitted from areas other than the diseased site is displayed as a background image other than the diseased site etc., i.e., as a background, in the fluorescence image. Furthermore, if the distance with respect to the scope 2 is too short, even a healthy site may be identified as a high-gradation region despite its faint fluorescence and may be displayed as a diseased site on the fluorescence image (hereinbelow, such a region is referred to as a "false positive site").

Figure 4B:
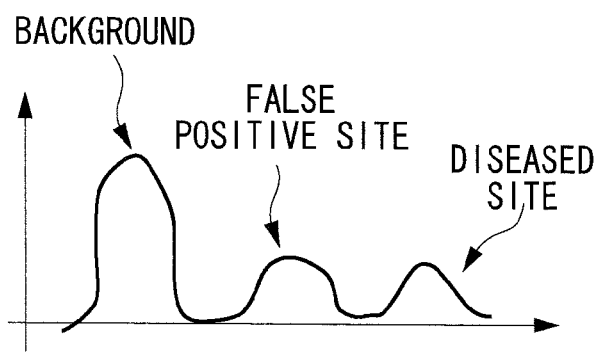
FIG. 4B is a histogram showing the relationship between the gradation values of pixels and the frequencies in the entire image in the fluorescence image in FIG. 4A.
Figure 5A:
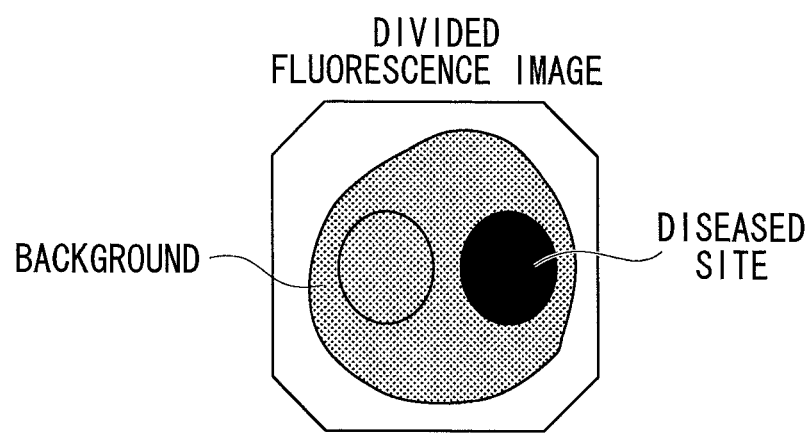
FIG. 5A is a diagram showing an example of a divided fluorescence image.
Figure 5B:
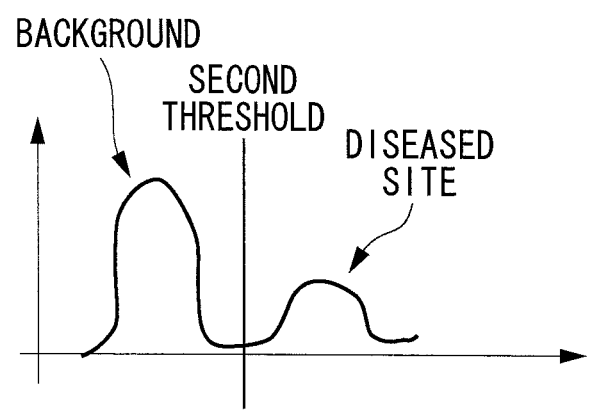
FIG. 5B is a histogram showing the relationship between the gradation values of pixels and the frequencies in the entire image in the divided fluorescence image in FIG. 5A.
Figure 6A:
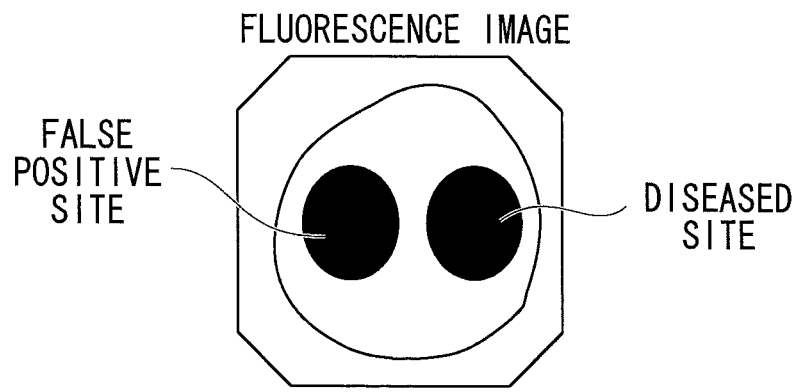
FIG. 6A is a diagram showing an example of a corrected fluorescence image, in which a background is removed.
Figure 6B:
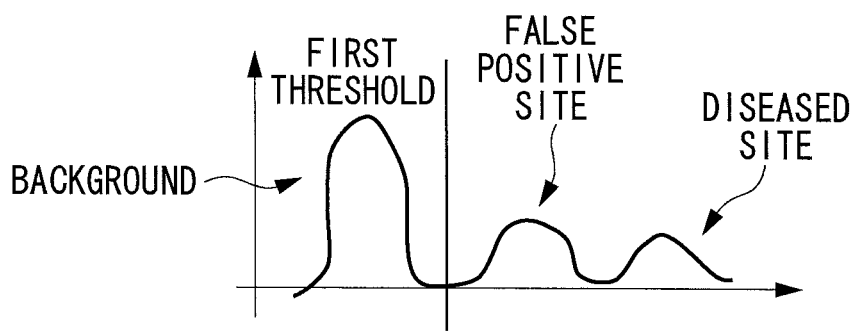
FIG. 6B is a histogram showing the relationship between the gradation values of pixels and the frequencies in the entire image in the fluorescence image in FIG. 6A.

As shown in FIGS. 4A and 4B, the fluorescence image is mainly composed of a diseased-site region, a false-positive-site region, and a background region surrounding them. In FIG. 4B, the horizontal axis indicates the gradation value, and the vertical axis indicates their frequencies in the entire corrected fluorescence image (FIGS. 5B and 6B too).

The fluorescence image and white-light image generated by the image generating portion 41 are sent to the dividing portion 43. In the dividing portion 43, the fluorescence image is divided by the white-light image to generate a divided fluorescence image, as shown in FIG. 5A. The generated divided fluorescence image is sent to the coordinate extracting portion 47 (step SA3).

As has been described above, because the influence of the observation distance and observation angle is reduced in the divided fluorescence image, the false-positive-site region, which exceeds the first threshold due to the influence of the observation distance and observation angle in the fluorescence image, does not exceed the second threshold and can be identified as a part of the background in the divided fluorescence image. As shown in FIGS. 5A and 5B, the divided fluorescence image is mainly composed of a diseased-site region having a higher gradation value than the second threshold and a background region including a false positive site having a gradation value lower than or equal to the second threshold.

In the coordinate extracting portion 47, the coordinates of the pixels of the divided fluorescence image, sent from the dividing portion 43, having a gradation value lower than or equal to the second threshold inputted from the second-threshold setting portion 45B are extracted, and the extracted coordinates of the pixels are sent to the fluorescence-image correcting portion 49 (step SA4). As a result, similarly to a region in the divided fluorescence image having a higher gradation value than the second threshold (second region), i.e., the diseased-site region, being extracted by the coordinate extracting portion 47, the second region is distinguished from a low-gradation region, such as a background.

In the fluorescence-image correcting portion 49, the gradation values of the pixels of the fluorescence image having a lower gradation value than the first threshold inputted from the first-threshold setting portion 45A are substituted with zero (step SA5). As a result, as shown in FIGS. 6A and 6B, the background of the fluorescence image is removed, and regions having a higher gradation value than the first threshold (first regions), i.e., a diseased-site region and a false-positive-site region, are extracted.

Figure 7:
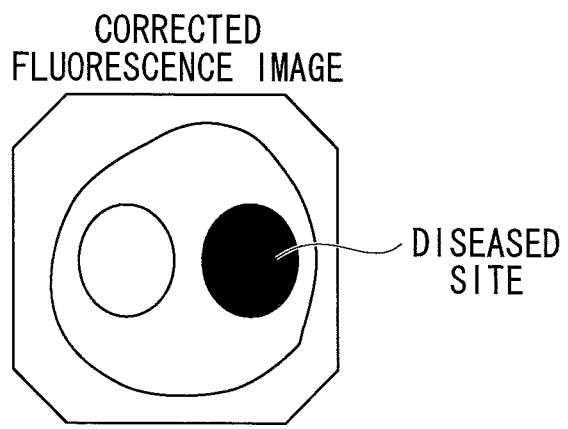
FIG. 7 is a diagram showing an example of a corrected fluorescence image.

Then, the fluorescence-image correcting portion 49 substitutes the gradation values of the pixels of the fluorescence image, in which the diseased-site region and the false-positive-site region are extracted, corresponding to the coordinates inputted from the coordinate extracting portion 47 with zero (step SA6). As a result, as shown in FIG. 7, the false-positive-site region in the fluorescence image is removed, and a corrected fluorescence image is generated, in which the diseased-site region, which is an overlap region of the first region in the fluorescence image and the second region in the divided fluorescence image, is extracted.

The generated corrected fluorescence image is sent to the monitor 50 to be displayed (step SA7). In this manner, when a fluorescence image and a white-light image of the next frame are generated, steps SA3 to SA7 are repeated, and a new corrected fluorescence image is displayed on the monitor 50.

As has been described above, with the fluorescence endoscope device 100 according to this embodiment, by removing the background of the fluorescence image with the first-region extracting portion 45A and by removing the false positive site of the fluorescence image with the second-region extracting portion 45B and the corrected-fluorescence-image generating portion 49, it is possible to generate a corrected fluorescence image, in which only the diseased site is extracted by suppressing not only the influence of the background lower than the first threshold but also the influence of the false positive site higher than the first threshold.

Furthermore, by generating a corrected fluorescence image on the basis of the fluorescence image, it is possible to suppress the influence of the factors that degrade the image quality, which are specific to the white-light image and are reflected in the divided image, such as the information about the shapes of an edge portion, a shadow portion, etc., of the observation target site X, and the information about the colors of a breeding site, a blood vessel, etc., different from the color of the surrounding portion. Thus, it is possible to obtain a precise corrected fluorescence image having few factors that degrade the image quality.

Although the coordinate extracting portion 47 extracts the coordinates of the pixels of the divided fluorescence image having a gradation value lower than or equal to the second threshold in this embodiment, the coordinate extracting portion 47 may instead directly extract the coordinate of the region (second region) of the divided fluorescence image having a higher gradation value than the second threshold. In this case, a corrected fluorescence image may be generated as a result of the coordinate extracting portion 47 outputting the coordinates of the second region to the fluorescence-image correcting portion 49 and as a result of the fluorescence-image correcting portion 49 substituting the gradation values of the pixels of the fluorescence image, in which the first region is extracted, other than the pixel corresponding to the coordinate of the second region (overlap region) with zero.

Furthermore, although the fluorescence-image correcting portion 49 substitutes the gradation values of the pixels of the fluorescence image having a lower gradation value than the first threshold with zero in the this embodiment, it is only necessary that the first region of the fluorescence image having a gradation value higher than the first threshold be extracted. Thus, for example, in the fluorescence image, the first region and the region having a lower gradation value than the first threshold may be displayed in different colors. Furthermore, although the fluorescence-image correcting portion 49 substitutes the gradation values of the pixels of the fluorescence image having the same coordinates as the coordinates extracted by the coordinate extracting portion 47 with zero, it is only necessary that the overlap region of the first region of the fluorescence image and the second region of the divided fluorescence image having a gradation value higher than the second threshold be extracted from the fluorescence image. Thus, for example, the overlap region and the region other than the overlap region may be displayed in different colors.

This embodiment may be modified as follows.

Figure 8:
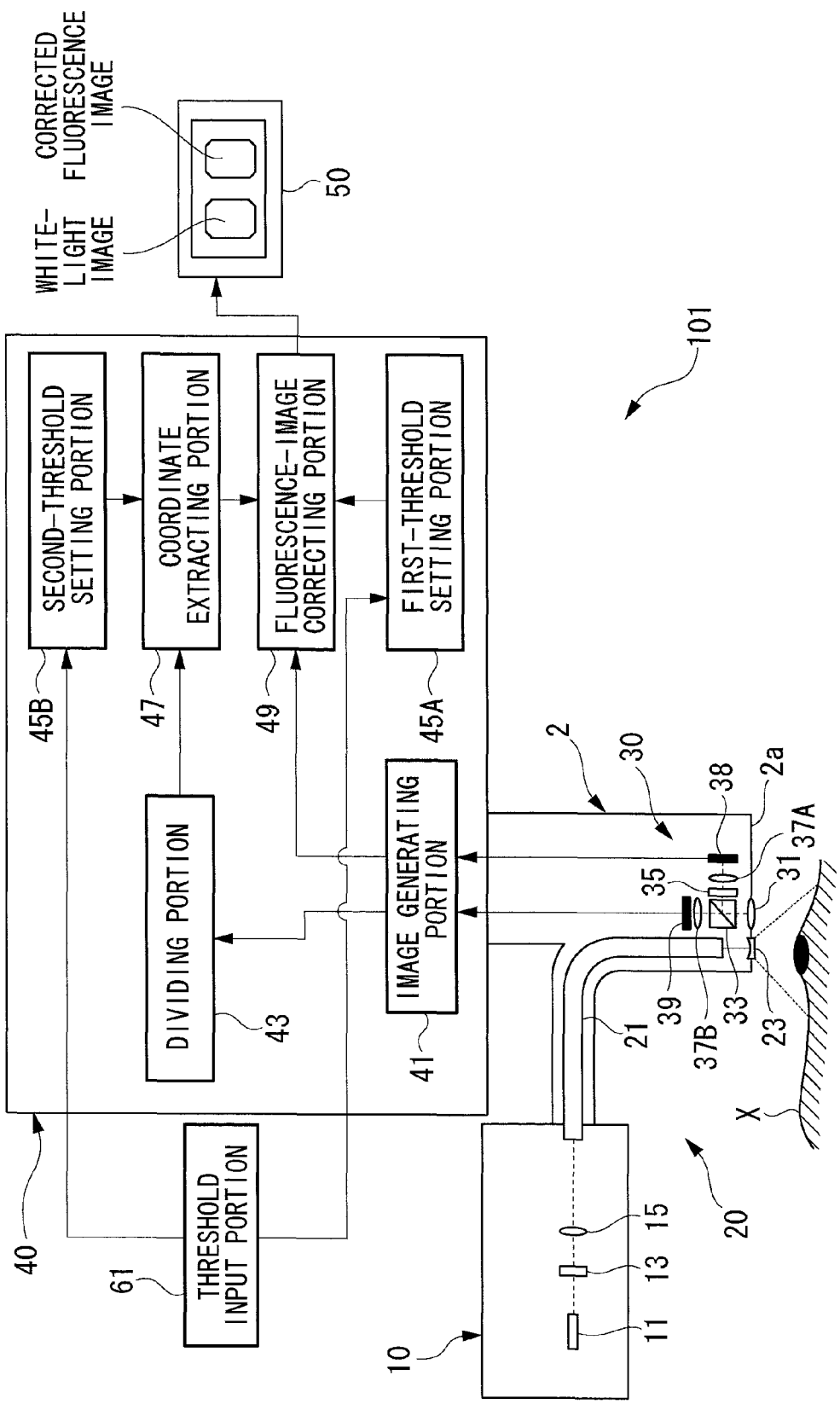
FIG. 8 is a schematic block diagram of a fluorescence endoscope device according to a first modification of an embodiment of the present invention.

For example, although the first-threshold setting portion 45A and the second-threshold setting portion 45B set the respective thresholds in this embodiment, in a first modification, as shown in FIG. 8, a fluorescence endoscope device 101 may include a threshold input portion 61 for inputting the respective thresholds, and an operator may activate the threshold input portion 61 to manually input the first threshold and the second threshold to the first-threshold setting portion 45A and the second-threshold setting portion 45B. By doing so, the operator can set desired thresholds according to the observation object and the observation method.

Figure 9:
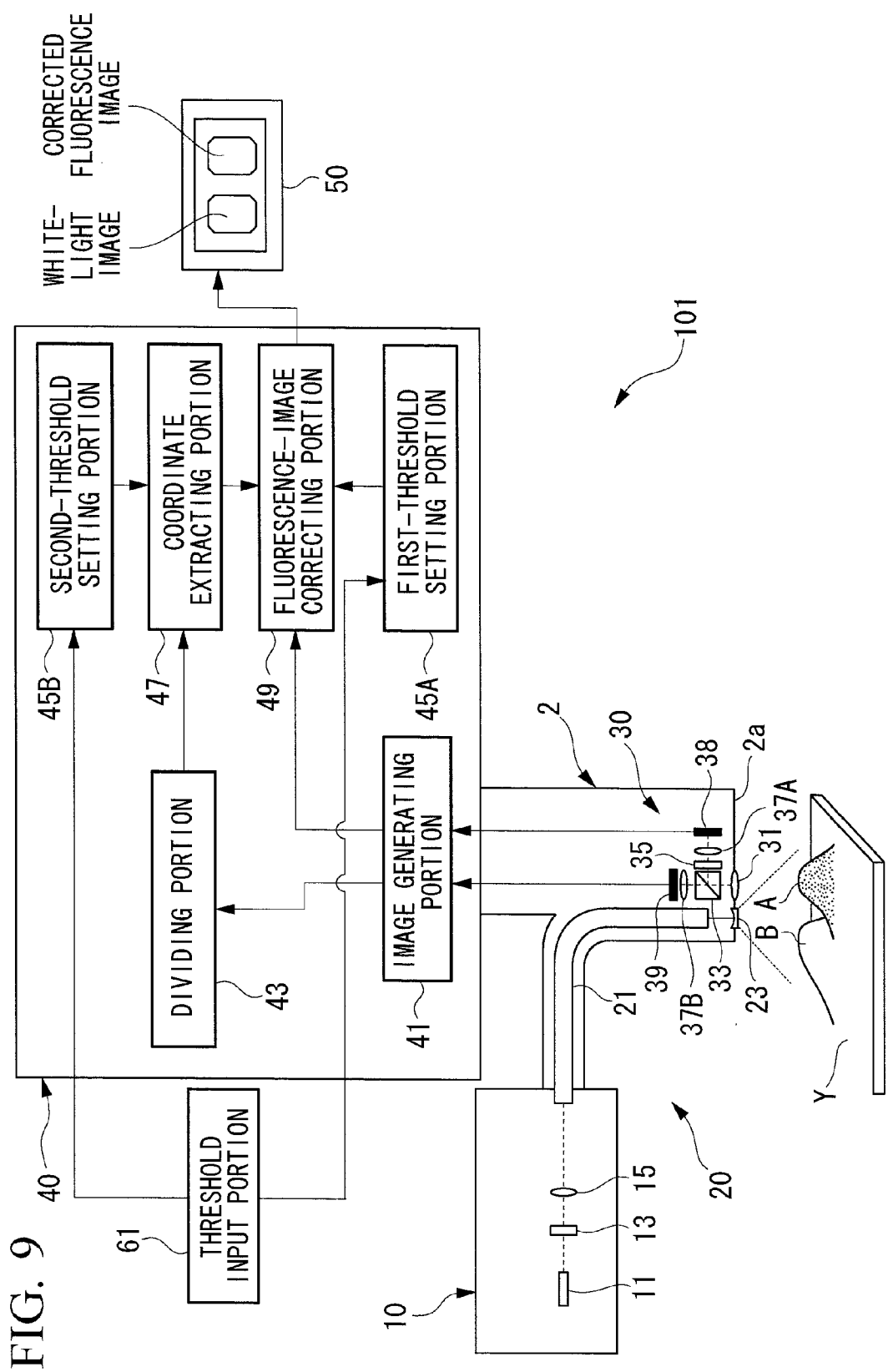
FIG. 9 is a schematic block diagram of the fluorescence endoscope device according to the modification in FIG. 8.

In this modification, for example, as shown in FIG. 9, a phantom (standard sample) Y may be observed to set the first threshold and the second threshold. Examples of the phantom Y include a phantom having such a shape that a flat-plate-like base has two projections A and B, the projection A emitting fluorescence having a higher intensity than the surrounding area and showing a gradation value of 2000 on the fluorescence image, and the projection B emitting fluorescence having substantially the same intensity as the base and showing a gradation value of 1000 on the fluorescence image, when observed under predetermined observation conditions (distance and angle).

Figure 10:
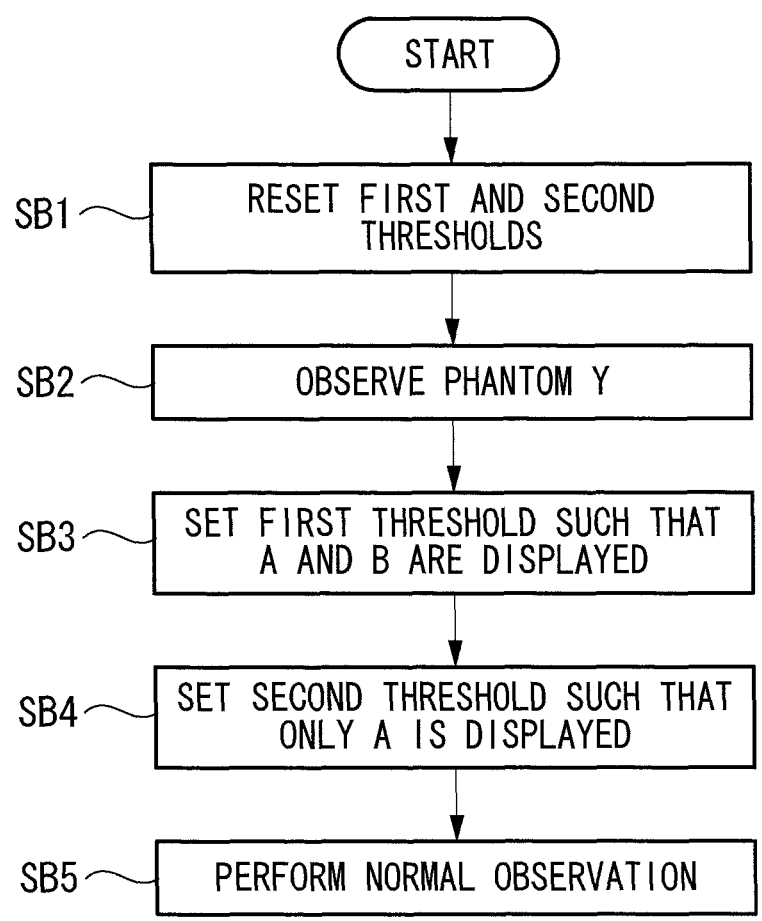
FIG. 10 is a flowchart showing the operation of the fluorescence endoscope device in FIG. 9.

In this case, for example, as shown in the flowchart in FIG. 10, the predetermined first threshold and second threshold are reset (step SB1), and the observation is started by disposing the phantom Y such that the observation distance between the scope 2 and the projections A and B is about 70% of the distance between the scope 2 and the base (step SB2). Because the fluorescence intensity is inversely proportional to the square of the observation distance, if observation is performed under the above-described predetermined observation conditions, the image generating portion 41 generates a fluorescence image in which the base has a gradation value of 1000, the projection A has a gradation value of about 4000, and the projection B has a gradation value of about 2000. On the other hand, in the divided fluorescence image generated by the dividing portion 43, because the influence of the observation distance is reduced, the base and the projection B each have a gradation value of 1000, and the projection A has a gradation value of about 4000.

Next, the first-threshold setting portion 45A sets the first threshold to, for example, 1500, so that only the projections A and B are displayed on the fluorescence image (step SB3). Furthermore, the second-threshold setting portion 45B sets the second threshold to 1500, so that the projection B, along with the base, is identified to be lower than or equal to the second threshold (step SB4). By setting the respective thresholds in this way, it is possible to generate a corrected fluorescence image in which the base of the phantom Y, shown as the background, and the projection B, shown as the false positive site, are removed, and in which the projection A is shown. Accordingly, the observation target site X inside the body of a living body may be observed by using the first threshold and the second threshold (step SB5).

By preparing a plurality of phantoms having shapes corresponding to parts to be observed, precisely thresholds for various observation objects can be set. For example, when the large intestine is to be observed, a phantom having a tubular shape similar to the lumen of the large intestine may be used to set thresholds. Furthermore, when, for example, the stomach is to be observed, a hollow phantom having a relatively large space may be used to set the thresholds.

Figure 11:
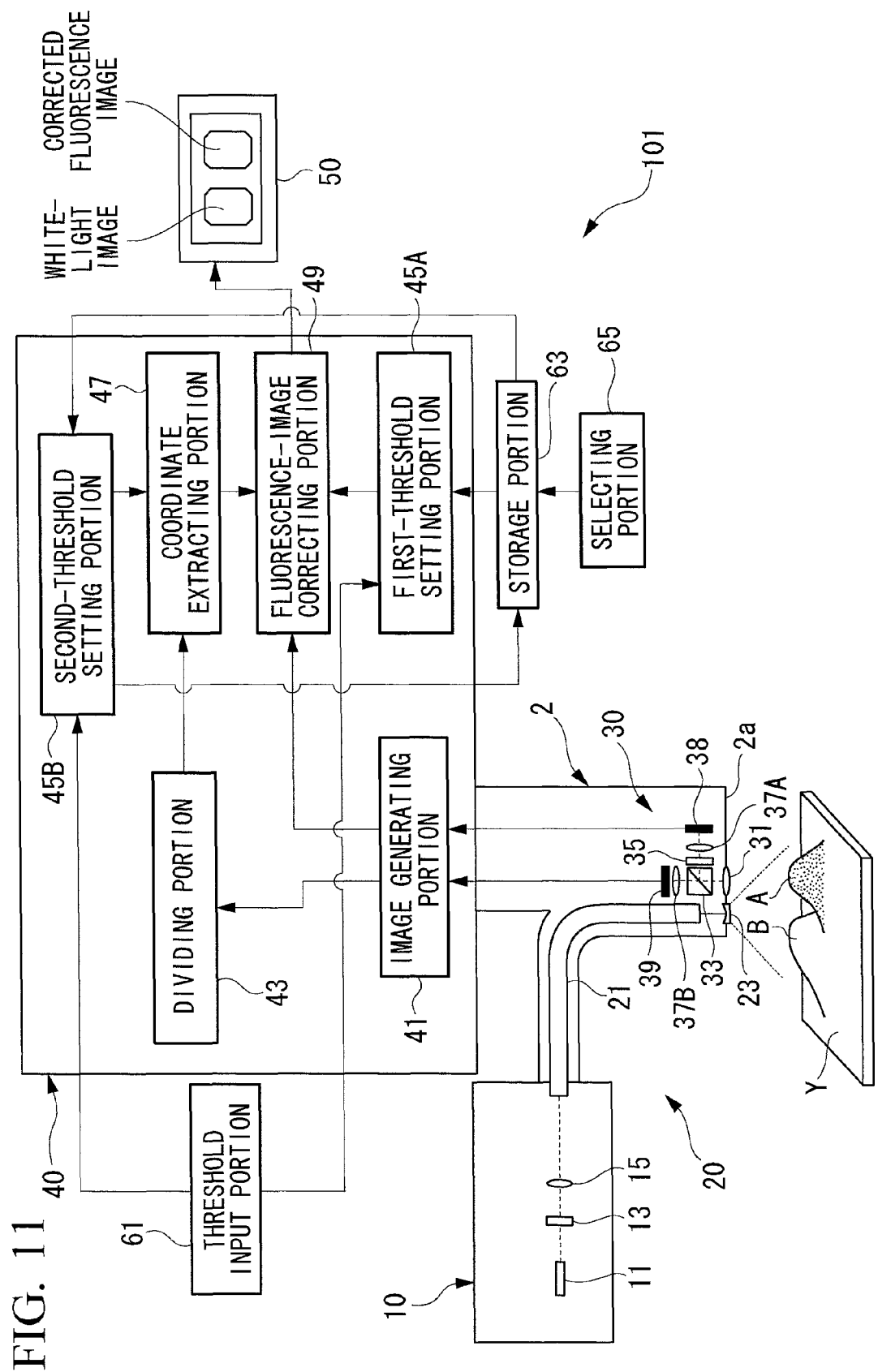
FIG. 11 is a schematic block diagram of a fluorescence endoscope device according to the modification in FIG. 9.

In this modification, for example, as shown in FIG. 11, the fluorescence endoscope device 101 may include a storage portion 63 that stores the thresholds set by using a plurality of the phantoms Y, and a selecting portion 65 that selects the threshold corresponding to each phantom, stored in the storage portion 63. By doing so, a precise threshold can be easily set when observation is performed under the same observation conditions, thereby simplifying the operation.

Figure 12:
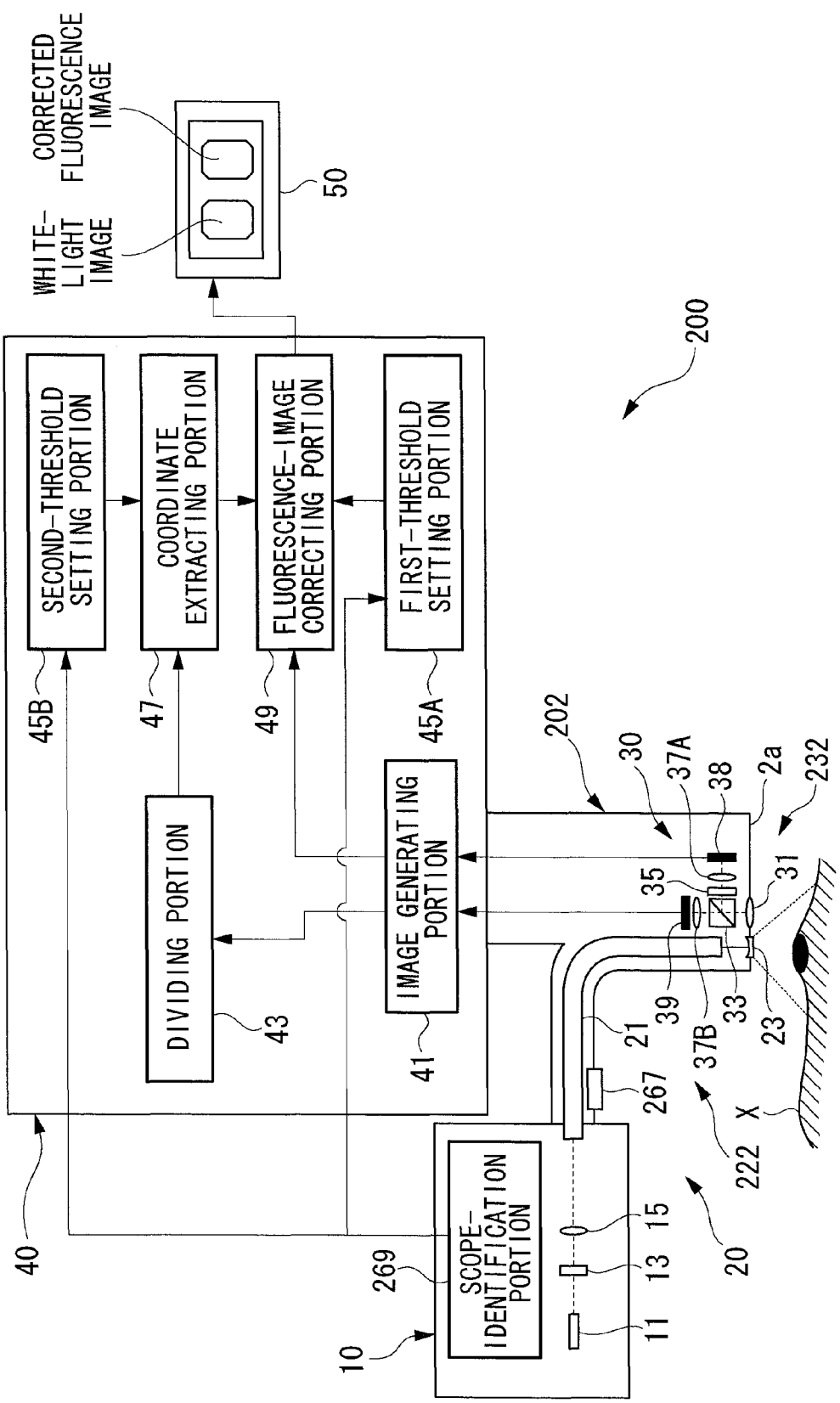
FIG. 12 is a schematic block diagram of a fluorescence endoscope device according to a second modification of an embodiment of the present invention.

In a second modification, as shown in FIG. 12, a fluorescence endoscope device 200 may include a scope (endoscope scope) 202 that has an IC chip 267 storing scope information and that can be inserted and withdrawn, and the light source 10 may have a scope-identification portion 269 that determines the scope information stored in the IC chip 267. Examples of the scope information include the number of light-emitting portions 222, composed of a light-guide fiber 21 and a spreading lens 23, and the observation angle of a light-receiving portion 232, composed of the light-emitting portion 222 and the objective lens 31.

In this case, when the scope 202 is connected to the light source 10, the scope-identification portion 269 may read out the scope information stored in the IC chip 267 and output the scope information to the first-threshold setting portion (threshold setting portion) 45A and the second-threshold setting portion (threshold setting portion) 45B, and the first-threshold setting portion 45A and the second-threshold setting portion 45B may set the first threshold and the second threshold on the basis of the scope information. By doing so, it is possible to set practical first and second thresholds for the endoscope scopes 202 each having different uses and specifications to obtain a more precise corrected fluorescence image according to the observation object and the observation method.

In this modification, similarly to the first modification, the phantom Y may be observed to set the first threshold and the second threshold.

Figure 13:
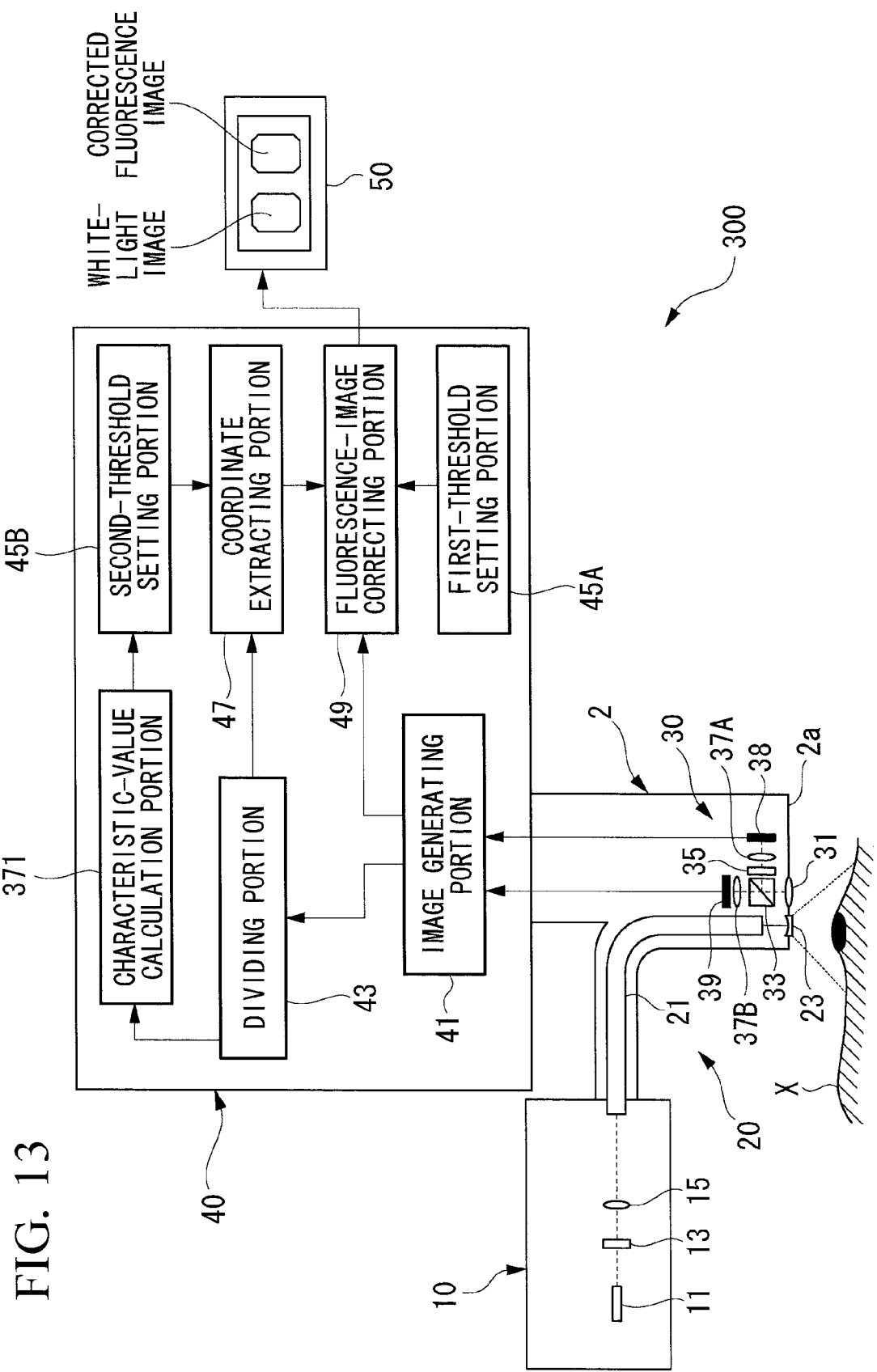
FIG. 13 is a schematic block diagram of a fluorescence endoscope device according to a third modification of an embodiment of the present invention.

In a third modification, as shown in FIG. 13, a fluorescence endoscope device 300 may include a characteristic-value calculation portion 371 that calculates the average gradation value, m, of the pixels of the divided fluorescence image and the standard deviation, σ, of that gradation value, and the second-threshold setting portion 45B may set a second threshold S on the basis of the sum of the average gradation value m and the standard deviation σ, as shown in Formula 1 below.

{Formula 1}

$$S = a \times m + b \times \sigma \qquad (1)$$

where a and b are coefficients.

When an observation target site X inside the body of a living body is observed using the fluorescence endoscope device 300 according to this modification, as shown in the flowchart in FIG. 14, first, the characteristic-value calculation portion 371 may set coefficients a and b in the Formula 1 above (for example, a=b=1) (step SC1), and the dividing portion 43 may output the generated divided fluorescence image to the characteristic-value calculation portion 371 and the coordinate extracting portion 47 (step SC2). Furthermore, the characteristic-value calculation portion 371 may calculate the average gradation value m of the entire divided fluorescence image and the standard deviation σ thereof and output them to the second-threshold setting portion 45B (step SC3), and the second-threshold setting portion 45B may set the second threshold S using Formula 1 and output it to the coordinate extracting portion 47 (step SC4). Steps SC5 to SC8 are the same as steps SA4 to SA7 in FIG. 2.

By doing so, it is possible to update the second threshold according to changes of the gradation values of the pixels of the divided fluorescence image or set a precise second threshold even when the gradation values of the pixels vary. Furthermore, it is possible to set a precise second threshold for each of the generated divided fluorescence images by absorbing the variation in the divided fluorescence image caused by the observation distance and observation variation. For example, coefficients a and b may be set such that they are inversely proportional to the estimated ratio of the diseased site in the divided fluorescence image. By doing so, it is possible to limit the minimum value and maximum value of the second threshold on the basis of the ratio of the region of pixels having a high-gradation value in the divided fluorescence image.

Although the second-threshold setting portion 45B sets the second threshold S on the basis of the sum of the average gradation value, m, of the entire divided fluorescence image and the standard deviation, σ, of that gradation value in this modification, for example, the first-threshold setting portion 45A may also set the first threshold on the basis of the sum of the average gradation value of the entire fluorescence image and the standard deviation of that gradation value. In this case, similarly to the second threshold S, the characteristic-value calculation portion 371 may calculate the average gradation value of the entire fluorescence image and the standard deviation thereof and output them to the first-threshold setting portion 45A.

In this modification, the fluorescence endoscope device 300 may include a coefficient input portion (not shown) for inputting coefficients a and b to the characteristic-value calculation portion 371.

Furthermore, although the second-threshold setting portion 45B sets the second threshold S on the basis of the sum of the average gradation value, m, of the pixels of the divided fluorescence image and the standard deviation, σ, of that gradation value in this modification, the second-threshold setting portion 45B may instead set the second threshold S on the basis of the sum of the modal gradation value or median gradation value of the pixels and the standard deviation, σ, of that gradation value. For example, if the observation distance increases, the number of portions having a gradation value of 0 may increase in the corrected fluorescence image. In such a case, the average gradation value of the pixels is smaller than the gradation value resulting from the fluorescence from the background. Accordingly, by using the modal gradation value or median gradation value of the pixels instead of the average gradation value of the pixels, it is possible to reduce the influence of the pixels having a gradation value of 0, and to reflect the fluorescence intensity from the background more appropriately.

REFERENCE SIGNS LIST

10: light source
41: image generating portion (fluorescence-image acquisition portion and reference-image acquisition portion)
43: dividing portion (divided-fluorescence-image generating portion)
45A: first-threshold setting portion
45B: second-threshold setting portion
47: coordinate extracting portion (second-region extracting portion)
49: fluorescence-image correcting portion (first-region extracting portion, corrected-fluorescence-image generating portion)
50: monitor (display portion)
61: threshold input portion
100, 101, 200, 300: fluorescence endoscope device
202: endoscope scope
222: light-emitting portion
232: light-receiving portion

The invention claimed is:

1. A fluorescence endoscope device comprising:
   a light source configured to emit excitation light and illumination light for irradiating a subject;
   a fluorescence-image acquisition sensor configured to capture image information of fluorescence generated at the subject due to the irradiation with the excitation light from the light source;
   a reference-image acquisition sensor configured to capture image information of return light returning from the subject due to the irradiation with the illumination light from the light source; and
   a processor comprising hardware, the processor implementing:
      an image generating portion configured to generate a fluorescence image based on the image information of the fluorescence, and to generate a reference image based on the image information of return light;
      a divided-fluorescence-image generating portion configured to divide the fluorescence image by the reference image to generate a divided fluorescence image, wherein effects of one or both of an observation distance and observation angle on intensity value is reduced in the divided fluorescence image as compared to the fluorescence image;
      a first-region extracting portion configured to extract a first region or first regions of the fluorescence image, the first region or first regions having a gradation value higher than a first threshold gradation value, wherein the first threshold gradation value is set to distinguish between:
         pixels in the fluorescence image having gradation values representing a first background site; and
         pixels in the first region or first regions of the fluorescence image having gradation values representing a target site and pixels in the first region or first regions of the fluorescence image having gradation values representing the effects of one or both of observation distance and observation angle;
      a second-region extracting portion configured to extract a second region or second regions of the divided fluorescence image, the second region or second regions having a gradation value higher than a second threshold gradation value different from the first threshold gradation value, wherein the second threshold gradation value is set to distinguish between:
         pixels in the divided fluorescence image having gradation values representing a second background site; and
         pixels in the second region or second regions of the divided fluorescence image having gradation values representing the target site; and
      a corrected-fluorescence-image generating portion configured to:
         extract, from the fluorescence image, an overlap region where the first region or first regions of the fluorescence image overlaps the second region or second regions of the divided fluorescence image; and
         generate a corrected fluorescence image in which the overlap region is identified.

2. The fluorescence endoscope device according to claim 1, further comprising a threshold input device configured to receive an input of the first threshold gradation value and the second threshold gradation value.

3. The fluorescence endoscope device according to claim 1, wherein the processor further implements:
   a first-threshold setting portion configured to set the first threshold gradation value on the basis of a sum of an average gradation value of each of pixels of the fluorescence image and a standard deviation of that gradation value.

4. The fluorescence endoscope device according to claim 1, wherein the processor further implements:
   a second-threshold setting portion configured to set the second threshold gradation value on the basis of a sum of an average gradation value of each of pixels of the divided fluorescence image and a standard deviation of that gradation value.

5. The fluorescence endoscope device according to claim 1, wherein the processor further implements:
   a first-threshold setting portion configured to set the first threshold gradation value on the basis of a sum of a modal gradation value of each of pixels of the fluorescence image and a standard deviation of that gradation value.

6. The fluorescence endoscope device according to claim 1, wherein the processor further implements:
   a second-threshold setting portion configured to set the second threshold gradation value on the basis of a sum of a modal gradation value of each of pixels of the divided fluorescence image and a standard deviation of that gradation value.

7. The fluorescence endoscope device according to claim 1, wherein the processor further implements:
a first-threshold setting portion configured to set the first threshold gradation value on the basis of a sum of a median gradation value of each of pixels of the fluorescence image and a standard deviation of that gradation value.

8. The fluorescence endoscope device according to claim 1, wherein the processor further implements:
a second-threshold setting portion configured to set the second threshold gradation value on the basis of a sum of a median gradation value of each of pixels of the divided fluorescence image and a standard deviation of that gradation value.

9. The fluorescence endoscope device according to claim 1, further comprising:
an endoscope insertion portion configured to be inserted into a body cavity, the endoscope insertion portion comprising:
a light guide fiber configured to guide the excitation light and the illumination light emitted by the light source and to irradiate the subject with the guided excitation light and the guided illumination light;
the fluorescence-image acquisition sensor; and
the reference-image acquisition sensor,
wherein the processor further implements:
a threshold setting portion configured to set the first threshold gradation value and the second threshold gradation value on the basis of information about the light guide fiber, the fluorescence-image acquisition sensor, and the reference-image acquisition sensor.

* * * * *